United States Patent
Meek et al.

(10) Patent No.: US 6,430,259 B2
(45) Date of Patent: Aug. 6, 2002

(54) MEDICAL APPARATUS PROVIDED WITH A COLLISION DETECTOR

(75) Inventors: Gerrit Jan Meek; Cornelis Martinus Van Doorn; Wilhelmus Hubertus Baaten; Casparus Willibrordus Kruijer, all of Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/741,660

(22) Filed: Dec. 19, 2000

(30) Foreign Application Priority Data

Dec. 22, 1999 (EP) .............................. 99204472

(51) Int. Cl.⁷ ................................ H05G 1/54
(52) U.S. Cl. ........................................ 378/117; 378/94
(58) Field of Search ................................. 378/4, 19, 20, 378/114, 117, 91, 207, 209; 600/407, 425, 427

(56) References Cited

U.S. PATENT DOCUMENTS

| | | | |
|---|---|---|---|
| 4,448,200 A | * 5/1984 | Brooks et al. ............... 600/425 |
| 5,097,495 A | 3/1992 | Gary et al. ................... 378/117 |
| 5,570,770 A | * 11/1996 | Baaten et al. ............... 192/147 |
| 5,671,266 A | * 9/1997 | Linhart ......................... 378/175 |
| 5,878,112 A | * 3/1999 | Koertge ........................ 378/209 |
| 5,883,935 A | * 3/1999 | Habraken et al. ............ 378/117 |

FOREIGN PATENT DOCUMENTS

| | | | |
|---|---|---|---|
| DE | 4041294 A1 | 7/1991 | ............ A61B/6/00 |
| EP | 046295 A1 | 6/1990 | ............ A61B/6/00 |

OTHER PUBLICATIONS

Kitada Yoshitaka, "Prescaler Circuit", May 1983, Abstracts of Japan.

* cited by examiner

Primary Examiner—David P. Porta
Assistant Examiner—Therese Barber
(74) Attorney, Agent, or Firm—John Vodopia

(57) ABSTRACT

A medical apparatus for (radiation) diagnosis or therapy can be provided with moving parts 6. Such an apparatus must be provided with a collision detection device 26, 28, 30. A known collision sensor measures the supply current for the drive motor and hence induces a high degree of inaccuracy in the collision detection. According to the invention the force applied to the moving part (image intensifier 6) is measured directly on the relevant part so as to be compared with an expected value, an alarm signal being generated when a threshold value for the difference is exceeded. The expected value is calculated while taking into account all movement and acceleration parameters of the apparatus. The expected values can be calculated in advance and stored in a look-up table or can be calculated, preferably while using a model of the apparatus, during operation of the apparatus.

24 Claims, 4 Drawing Sheets

MEDICAL APPARATUS PROVIDED WITH A COLLISION DETECTOR

BACKGROUND OF THE INVENTION

1. Field of the Invention

The invention relates to an apparatus for medical diagnosis and/or therapy which includes drive means for driving at least one movable part of the apparatus and a detection device for detecting the presence of an object that is in contact with the moving part of the apparatus, which detection device includes:

sensor means for detecting an instantaneous force exerted on the movable part, comparison means for comparing said force with a value expected for said force that is available in the apparatus, which comparison means are arranged to produce an alarm signal when a predetermined difference between said force and said expected value is exceeded, and response means for initiating a reaction by the drive means in response to the alarm signal.

2. Description of the Related Art

An apparatus of this kind is known from U.S. Pat. No. 5,570,770.

Generally speaking, an apparatus for medical diagnosis and/or therapy may be provided with a radiation emitter and a radiation receiver. An example in this respect is formed by a medical X-ray apparatus provided with an X-ray source and an X-ray receiver which is usually referred to as an image intensifier. These two elements are arranged at some distance from one another, the patient to be examined or treated being positioned between the X-ray source and the image intensifier. The X-ray source and the image intensifier are positioned relative to the body of the patient such that an image can be formed of the desired cross-section of the body (the object). The orientation and the position of such apparatus can often be adjusted by means of drive means in the form of a motor drive. Generally speaking, in the context of the present invention the term object is to be understood to mean the body of a patient to be examined or another body to be examined, the body or a part of the body of a person operating the apparatus, parts of the apparatus itself (for example, the patient table) or of neighboring apparatus, or other obstacles that could enter the path of movement of the parts of the apparatus.

Such apparatus are often provided with a so-called C-arm, that is, a circular support which is rotatable in its own plane (that is, about an axis extending perpendicularly to the plane in which the C-arm is situated) by way of a trackway, the plane of said C-arm itself being rotatable about an axis situated in said plane. In many cases there is also a large number of other possibilities for displacement.

During use of the apparatus it is important that a movable part, for example the image intensifier, comes close to the object to be examined in order to achieve the desired clarity of the image. The image intensifier has a comparatively large front surface for receiving the X-rays and any point on this front surface or on its circumference could come into contact with the object to be examined. Such a collision may occur in any direction of movement of the image intensifier. This is undesirable and, therefore, an apparatus of this kind is provided with a detection device for detecting the presence of an object situated in the vicinity of or in contact with the movable part of the apparatus.

It is important to include such a detection device notably in motor-driven apparatus. When contact is detected between the movable part of the apparatus and an object, the movement of said (part of the) apparatus can be stopped so as to minimize the seriousness of the consequences of a collision.

The cited U.S. Pat. No. 5,570,770 discloses a medical X-ray apparatus that is provided with an electrical detection device for detecting the presence of an object that is in contact with a movable part of the apparatus. The sensor means in such an apparatus are arranged to measure the current and/or the power taken up by the driving motor. These quantities form an indication of the instantaneous force exerted on the movable part; this instantaneous value can be compared with a value expected for said force that is stored in the apparatus. When the difference between the instantaneous value and the expected value exceeds a predetermined threshold value, it is assumed that the movement of the movable part is impeded by an object and hence that a collision takes place. Consequently, an alarm signal is generated and in response thereto the driving motor is made to react; for example, the motor can be stopped and braked or only stopped; it can also be made to perform a retracting motion after stopping.

Because the sensor means in the known apparatus measure the current and/or power taken up by the driving motor, the determination of the instantaneous force exerted on the movable part is inaccurate and not very well reproducible. On the one hand, this may lead to the conclusion that a collision occurs even though there is no such collision, or on the other hand, to late detection of an actual collision occurring. Evidently, both situations are undesirable for medical equipment.

SUMMARY OF THE INVENTION

It is an object of the invention to provide an apparatus of the kind set forth in which a state of collision can be determined in a more accurate and better reproducible manner. To this end, the apparatus according to the invention is characterized in that the sensor means include a force sensor which is arranged in such a position that it detects directly the instantaneous force exerted on the movable part. The invention is based on the recognition of the fact that said imperfections are due to the fact that a large number of intermediate parts for transmission and driving are present between the movable part of the apparatus and its drive. Each of said intermediate parts introduces friction, mass inertia, play and elastic deformation; moreover, such phenomena are highly dependent on the instantaneous position and acceleration of the movable parts and on the state of ageing of the apparatus. When the instantaneous force exerted on the movable part is determined without such an intermediate arrangement of these components, the effect thereof is eliminated.

The forces exerted on the movable part of the apparatus in a preferred embodiment are transferred to the apparatus via guide means that bear on one of the other parts of the apparatus, the force sensor being arranged in or directly on said guide means. The guide means notably include the bearing arrangement of a drive spindle for driving the movable part. In this embodiment an as direct as possible coupling is realized between the force sensor and the movable part.

In conformity with a further embodiment of the invention the apparatus is provided with state sensing means for determining the positional and/or motional state of the apparatus and the comparison means in the apparatus have available a data set of expected values, said data being a function of the positional and/or motional state of the apparatus. As a result of these steps a variety of variable effects exerted on the force to be determined can be taken into account, for example the effect of the force of gravity for different states of the apparatus. In this context the term "different states" is to be understood to mean all parameters defining the state of the relevant movable part of the apparatus. In the case of an image intensifier supported by a C-arm, therefore, this may be the angular rotation of the C-arm (in its own plane and about an axis situated in said plane) and the height adjustment of the image intensifier relative to its guide. These steps also enable other variable effects exerted on the force to be determined to be taken into account, for example, the acceleration of the various parts of the apparatus, again in different states of the apparatus. The assembly of such parameters constitutes the positional and/or motional state of the apparatus. Said state sensing means detect the positional state and/or motional state of the apparatus and the set of data thus obtained (that is, the instantaneous value of the positional state and/or motional state of the apparatus) then acts as a variable for the selection of the instantaneous expected value from the data set of expected values.

A further embodiment of the apparatus in accordance with the invention is provided with state sensing means for determining the positional and/or motional state of the apparatus, the comparison means in the apparatus being provided with processor means for calculating and presenting said expected value on the basis of a model of the apparatus and in dependence on the positional and/or motional state of the apparatus. These steps also enable the effects exerted on the force to be determined to be taken into account, said state sensing means determining the positional and/or motional state of the apparatus. The set of data presented by the state sensing means in this embodiment is applied to a processor whose software contains a model of the apparatus, that is, the equations necessary to calculate the expected value for the relevant force in dependence on said set of data. This embodiment offers the advantage that effects that vary in time, for example, frictional forces or play that change due to wear or elastic deformation that changes due to a reduced rigidity of components, can be readily adapted by modifying the relevant numerical values in the software. These values are, for example, the numerical values of the friction coefficients, the magnitude of the play and the elasticity moduli.

BRIEF DESCRIPTION OF THE DRAWINGS

The invention will be described in detail hereinafter with reference to the Figures in which corresponding elements are denoted by corresponding reference numerals. Therein.

DETAILED DESCRIPTION OF THE PREFERRED EMBODIMENT

Figure 1:
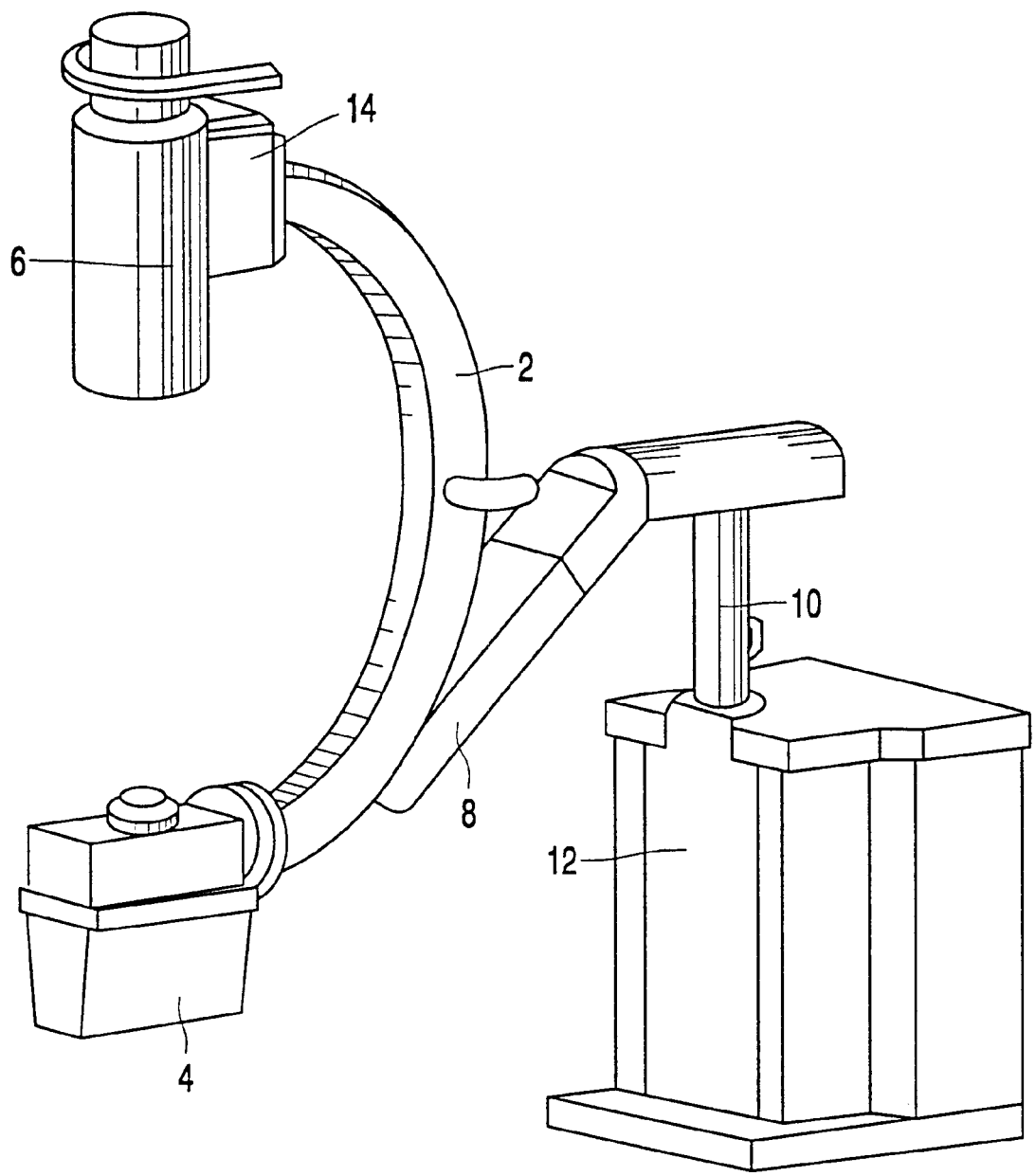
FIG. 1 is a general view of a known medical X-ray apparatus in which collision detection can take place.

FIG. 1 is a general view of a medical diagnostic and/or therapeutic apparatus in the form of an X-ray apparatus. The X-ray apparatus includes a support 2 on which an X-ray source 4 and an X-ray image intensifier 6 are mounted. The support is shaped as an arc of a circle so that it can be rotated about an axis extending perpendicularly to the plane of the arc by way of a trackway 8. This type of support is known as a C-arm; generally speaking, these arms are also rotatable about an axis situated in the plane of the arc of a circle. The mechanism for the latter motion is not shown in the figure. The assembly formed by the support 2 and the trackway 8 is also rotatable about a shaft 10. This shaft is mounted on a stand 12 which, if desired, may be constructed so as to be mobile. The X-ray source 4 and the X-ray detector 6 are preferably also displaceable relative to the support 2. In order to realize easy displacement of these components, they are provided with a motor drive which is not shown in the Figure. The object to be examined, in this case being the body of the patient to be examined or treated, is positioned on a table (not shown in the Figure) arranged between the image intensifier 6 and the X-ray source 4. Because of the described possibilities for movement of the C-arm 2, the image intensifier 6 and the X-ray source 4, these components can be aimed at the patient in all desired directions so that images can be formed of all desired cross-sections.

The movability of the image intensifier 6 relative to the support 2 is achieved by way of a coupling piece 14 along which the image intensifier can be displaced to and fro along an imaginary connecting line between the X-ray source 4 and the image intensifier 6. Because of their mobility, the movable parts, such as the image intensifier 6, can readily come into contact with the body of the patient to be examined or with other obstacles. It is desirable to detect such contact; therefore, the X-ray apparatus is provided with a detection device for the detection of the presence of an object that is in contact with the movable of the apparatus as will be described in detail hereinafter with reference to the following Figures.

Figure 2:
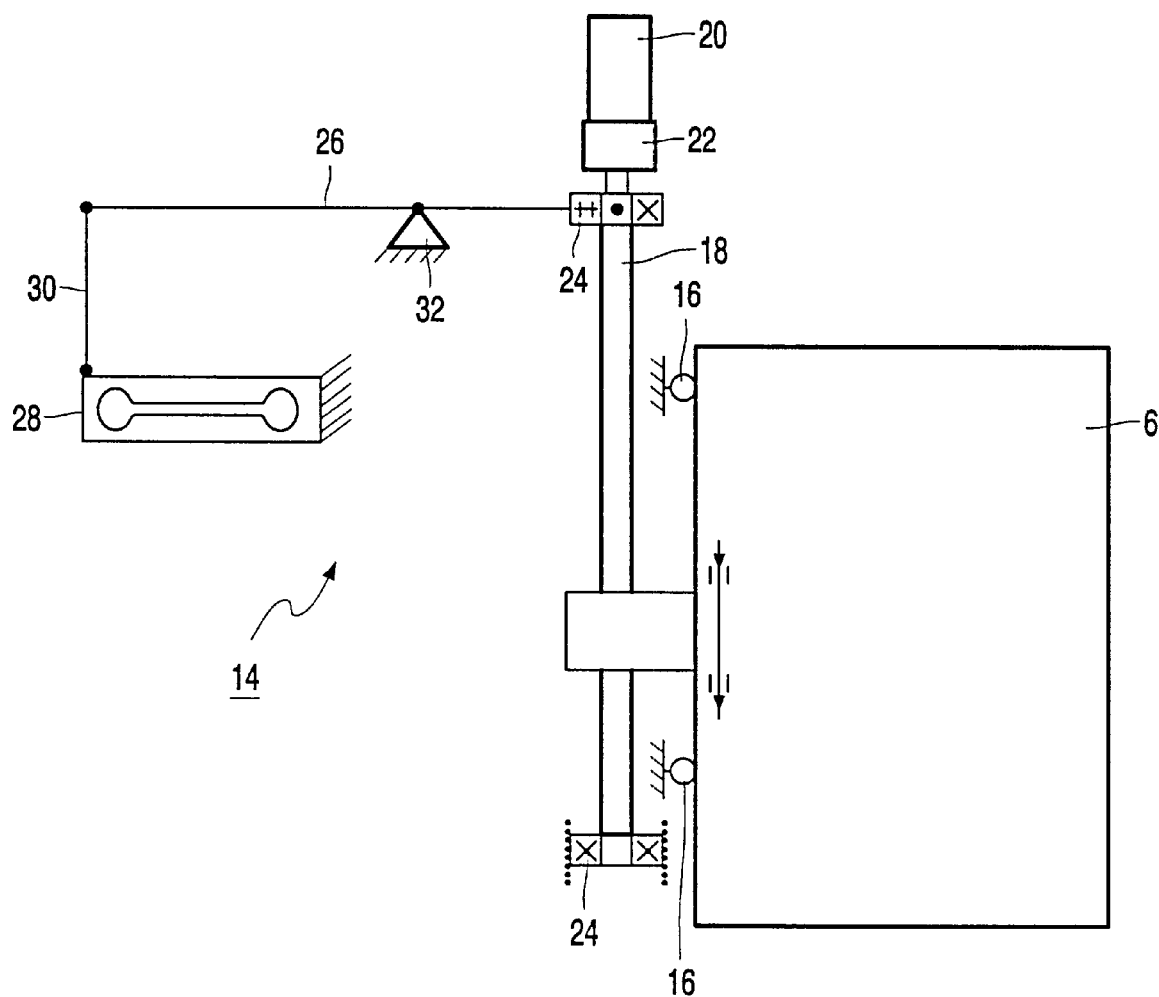
FIG. 2 is a simplified representation of the essential components involved in the force measurement in a medical X-ray apparatus.

FIG. 2 is a simplified view of the essential components involved in the force measurement in a medical X-ray apparatus. In this case the image intensifier 6 is chosen as the component of relevance. The image intensifier 6 is connected to the C-arm 2 by way of a coupling piece 14 (see FIG. 1) which includes a linear guide 16 that is driven by a spindle 18. The spindle is connected to a motor 20 which drives the spindle 18 via a gear box 22. The bearing 24 of the spindle is not rigidly connected to the frame (that is, the C-arm) of the X-ray apparatus, but is suspended from one end of a lever 26, the other end of which is held in place by a force sensor 28, if desired, via a transmission 30. The lever 26 pivots about a pivot 32, thus enabling adjustment of a transmission with a desired force ratio. The force sensor 28 as shown can measure the total force acting on the image intensifier 6 in the direction of the linear guide 16. Force measurements in directions other than that indicated in FIG. 2 can be performed in a similar manner.

Figure 3:
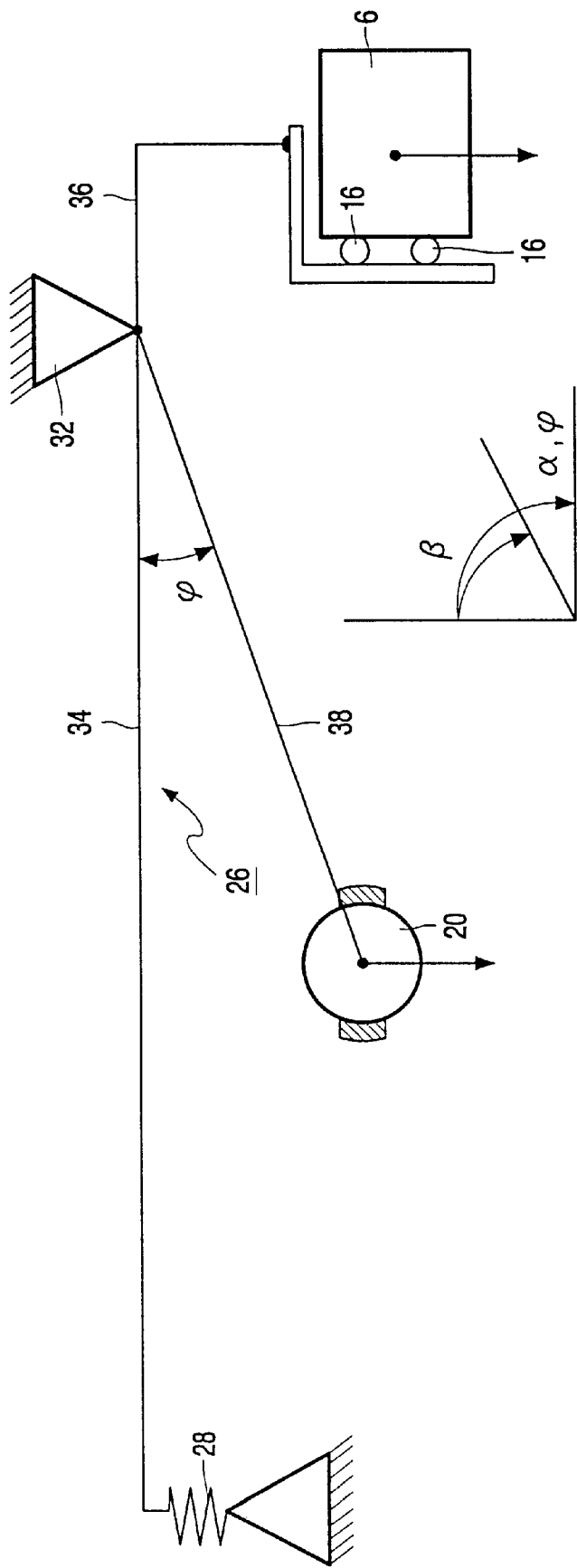
FIG. 3 is a diagrammatic representation of the force measurement in a medical X-ray apparatus.

FIG. 3 illustrates diagrammatically the force measurement in a medical X-ray apparatus. The weight of the image intensifier 6 and the forces acting thereon are measured by utilizing the principle of a scale with a sensor arm $L_s$ 34 and a load arm $L_1$ 36, the pivot 32 being connected to the frame of the apparatus. The drive motor 20 is connected, via a motor arm $L_m$ 38, to the lever 26 at an angle $\phi$. The end of the sensor arm 34 is connected to the force sensor 28, the other side of which is connected to the frame of the apparatus. It is assumed that the plane of the C-arm has been rotated through an angle $\beta$ relative to the vertical plane and that the lever 26 encloses an angle $\alpha$ relative to the horizontal direction. The force measured by the sensor is then determined by the sum of the following sub-forces: 1) the static gravitational forces acting on the image intensifier 6 and the drive motor 20; 2) the centrifugal forces occurring during the motion of the C-arm (rotating in its own plane as well as during rotation about an axis in said plane), and 3) acceleration forces on the image intensifier during the displacement along the linear guide. In these circumstances the measurement can be expressed in a formula as follows:

$$F_s(\alpha, \beta) = \frac{M_m \times L_m \times \cos(\alpha + \varphi) - M_1 \times L_1 \times \cos(\alpha)}{L_s} \times g \times \sin(\beta) \quad (1)$$

in which $M_m$ is the mass of the motor, $M_1$ is the mass of the image intensifier, $F_s$ is the force acting on the force sensor, and g is the acceleration of the force of gravity.

For the determination of the centrifugal force occurring both masses $M_1$ and $M_m$ should be transformed to an apparent mass $M'_1$ at the load side in conformity with the following expression (2):

$$M'_1 = M_1 - M_m \times \frac{L_m}{L_1} \quad (2)$$

As is known, the centrifugal force $F_{cp}$ acting on the force sensor is defined by the centripetal acceleration $a_{cp}$ (which itself is dependent on the angular speed ω) and the apparent mass $M_1'$. The expression for $F_{cp}$ then follows from the foregoing expression:

$$F_{cp} = \frac{M'_1 \times a_{cp} \times L_1}{L_s} \quad (3)$$

Finally, the acceleration forces a acting on the image intensifier during the displacement along the linear guide are given by:

$$F_a = M_1 \times a \quad (4)$$

Using the above expressions, the total force acting on the sensor can be determined as follows:

$$F_{tot} = F_s(\alpha,\beta) + F_{cp} + F_s \quad (5)$$

The expected value for the force acting on the force sensor can be determined by means of the latter expression (5).

Figure 4:
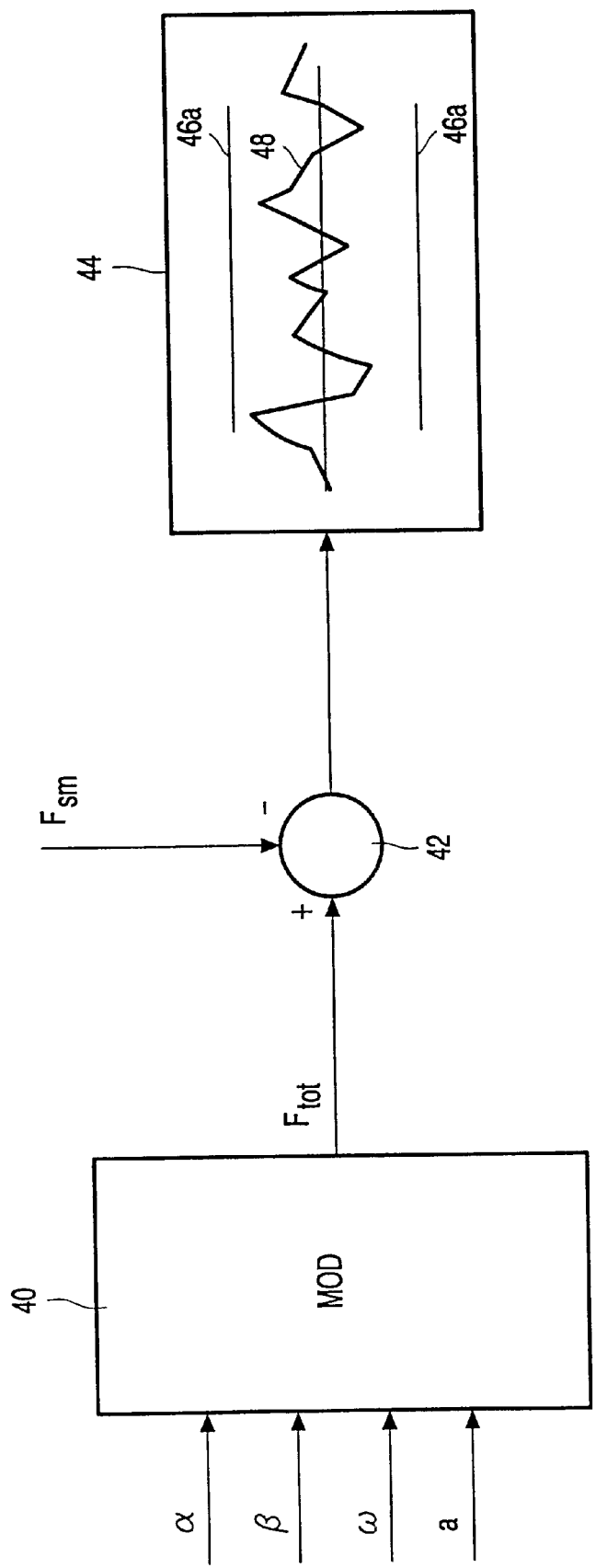
FIG. 4 is a diagrammatic representation of a model of the comparison of the instantaneously occurring force with the expected value.

FIG. 4 is a diagrammatic representation of a model of the comparison of the instantaneously occurring force with the expected value. The quantities that are relevant to the determination of the expected value for the force acting on the force sensor are the angle α, the angle β, the angular speed ω and the acceleration α. These quantities are transferred to a look-up table in which the expected value is stored as a function of said quantities, or to a processor 40 whose software contains a model of the apparatus, that is, the equations necessary to calculate the expected value for the relevant force in dependence on said set of data. Using said model, the processor 40 determines the expected value $F_{tot}$ which is subsequently applied to a differentiator 42 whose other input receives the force $F_{sm}$ measured on the sensor 28. The difference between these two quantities appears as a function of time 48 on the output of the differentiator, said difference being compared with a predetermined lower limit 46a and an upper limit 46b in a comparator 44. When said limits are exceeded, an alarm signal is generated and the driving motor can be made to react in response thereto; for example, it can be stopped and braked or only stopped or, moreover, after stopping a retracting motion can be initiated.

What is claimed is:

1. An apparatus for medical diagnosis or therapy which includes drive means for driving a movable part of the apparatus relative to an object being examined and a detection device for detecting contact between the movable part of the apparatus and the object, said detection device comprising:

sensor means for detecting an instantaneous force exerted on the movable part by the object, said sensor means including a force sensor arranged to directly detect the instantaneous force exerted on the movable part by the object, comparison means for comparing the detected force with an expected force value available in the apparatus, said comparison means being arranged to generate an alarm signal when a predetermined difference between the detected force and the expected force value is exceeded, and response means for initiating a reaction by said drive means in response to the alarm signal.

2. An apparatus as claimed in claim 1, further comprising guide means bearing on a part of the apparatus other than the movable part and arranged such that the forces exerted on the movable part of the apparatus are transferred to the apparatus via said guide means, said force sensor being arranged in or directly on said guide means.

3. An apparatus as claimed in claim 2, wherein said drive means comprise a drive spindle and said guide means include a bearing arrangement which supports said drive spindle.

4. An apparatus as claimed in claim 1, further comprising state sensing means for determining at least one of a positional and movement state of the apparatus, said comparison means having available a data set of expected force values, said data set being a function of at least one of the positional movement states of the apparatus as determined by said state sensing means.

5. An apparatus as claimed in claim 3, further comprising state sensing means for determining at least one of the positional and movement state of the apparatus, said comparison means including processor means for calculating and presenting the expected force value on the basis of a model of the apparatus and in dependence on at least one of the positional movement states of the apparatus as determined by said state sensing means.

6. An apparatus as claimed in claim 1, wherein said apparatus is an apparatus for medical X-ray examinations.

7. An apparatus as claimed in claim 1, wherein the movable part is an X-ray image detector.

8. An apparatus as claimed in claim 1, wherein said drive means comprise a spindle, a guide adapted to be coupled to the movable part and driven by said spindle, and a motor for driving said spindle such that motive force is transferred from said motor to said guide via said spindle.

9. An apparatus as claimed in claim 8, further comprising a bearing for supporting said spindle, said force sensor being coupled to said bearing.

10. An apparatus as claimed in claim 9, wherein said detection device further comprises a lever having a first fixed end and a second movable end, said lever pivoting about a pivot point between said first and second ends, said bearing being suspended at said second end of said lever.

11. An apparatus as claimed in claim 9, wherein said force sensor is arranged at said first end of said lever and holds said first end of said lever in a fixed position.

12. An apparatus as claimed in claim 9, wherein said detection device further comprises a transmission interposed between said first end of said lever and said force sensor.

13. An apparatus as claimed in claim 1, wherein said detection device further comprises a lever having a first fixed end and a second movable end, said lever pivoting about a pivot point between said first and second ends, said force sensor being coupled to said first end of said lever and said drive means being coupled to said second end of said lever.

14. An apparatus as claimed in claim 13, wherein said force sensor is arranged at said first end of said lever and holds said first end of said lever in a fixed position.

15. An apparatus as claimed in claim 13, wherein said detection device further comprises a transmission interposed between said first end of said lever and said force sensor.

16. An apparatus for medical diagnosis or therapy including a movable part, comprising:

drive means for driving the movable part, and detection means for detecting the presence of an object in contact with the movable part, said detection means comprising a force sensor for directly detecting an instantaneous force exerted on the movable part, comparison means coupled to said force sensor for comparing the detected force to an expected force value and generating an alarm signal based on the comparison of the detected force to the expected force value, and response means coupled to said comparison means for initiating a reaction by said drive means in response to the alarm signal.

17. An apparatus as claimed in claim 16, wherein said drive means comprise a spindle, a guide adapted to be coupled to the movable part and driven by said spindle, and a motor for driving said spindle such that motive force is transferred from said motor to said guide via said spindle.

18. An apparatus as claimed in claim 17, further comprising a bearing for supporting said spindle, said force sensing being coupled to said bearing.

19. An apparatus as claimed in claim 18, wherein said detection means further comprising a lever having a first fixed end and a second movable end, said lever pivoting about a pivot point between said first and second ends, said bearing being suspended at said second end of said lever.

20. An apparatus as claimed in claim 19, wherein said force sensor is arranged at said first end of said lever and holds said first end of said lever in a fixed position.

21. An apparatus as claimed in claim 19, wherein said detection means further comprise a transmission interposed between said first end of said lever and said force sensor.

22. An apparatus as claimed in claim 16, wherein said detection device further comprises a lever having a first fixed end and a second movable end, said lever pivoting about a pivot point between said first and second ends, said force sensor being coupled to said first end of said lever and said drive means being coupled to said second end of said lever.

23. An apparatus as claimed in claim 22, wherein said force sensor is arranged at said first end of said lever and holds said first end of said lever in a fixed position.

24. An apparatus as claimed in claim 22, wherein said detection device further comprises a transmission interposed between said first end of said lever and said force sensor.

* * * * *